United States Patent [19]

Umemoto et al.

[11] Patent Number: 4,779,987
[45] Date of Patent: Oct. 25, 1988

[54] METHOD OF SPECTROGRAPHICALLY MEASURING DENSITY OF PHOTOGRAPHIC NEGATIVE COLOR FILM

[75] Inventors: Choji Umemoto, Wakayama; Hideo Sato, Tokyo, both of Japan

[73] Assignees: Noritsu Kenkyu Center Co., Ltd., Wakayama; Jemco Inc., Kanagawa, both of Japan

[21] Appl. No.: 874,063

[22] Filed: Jun. 13, 1986

[30] Foreign Application Priority Data

Jun. 20, 1985 [JP] Japan .................................. 60-132974

[51] Int. Cl.4 .............................................. G01J 3/51
[52] U.S. Cl. ...................................... 356/404; 355/38; 355/77
[58] Field of Search ....................... 356/404, 443, 444; 355/38, 77

[56] References Cited

U.S. PATENT DOCUMENTS 4,668,082  5/1987  Terashita et al. ...................... 356/38

Primary Examiner—F. L. Evans
Attorney, Agent, or Firm—Larson & Taylor

[57] ABSTRACT

An improved method of spectrographically measuring density of a strip of photographic negative color film is disclosed. The method includes the steps of concurrently projecting an image of a photographic negative color film, having certain images recorded thereon, on each of a plurality of smaller divisional light beam receiving faces of an image receiving element with the aid of a plurality of projection optical systems. The optical systems include a color separating filter for separating projected light into three primary colors. The method further includes electrically scanning a number of photoelectric converting elements located on each light beam receiving faces, producing an output signal obtained by electrical scanning each face and storing the signal, and measuring relative density, degree of saturation and average density with respect to a part on the photographic negative color film corresponding to each of the light beam receiving face with reference to the stored signals. The smaller divisional light beam receiving faces are prepared by dividing a light beam receiving face having a large number of photoelectric converting elements arranged thereover in a two-dimensional plane and the number of the smaller divisional light beam receiving faces is same to that of the projection optical systems.

12 Claims, 7 Drawing Sheets

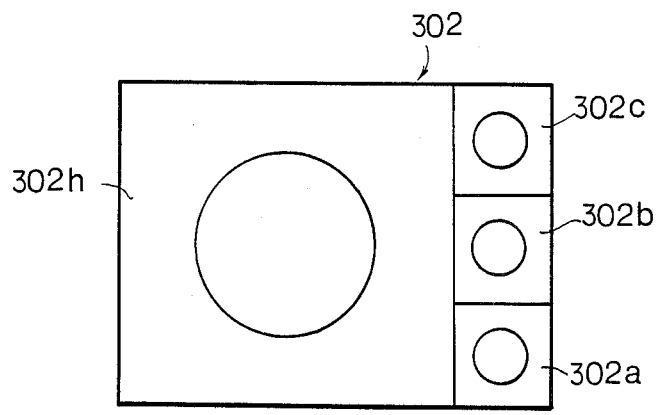
F I G. 9
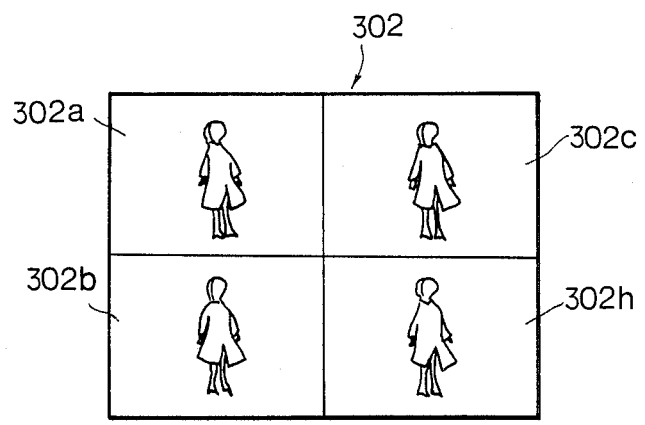
F I G. 10

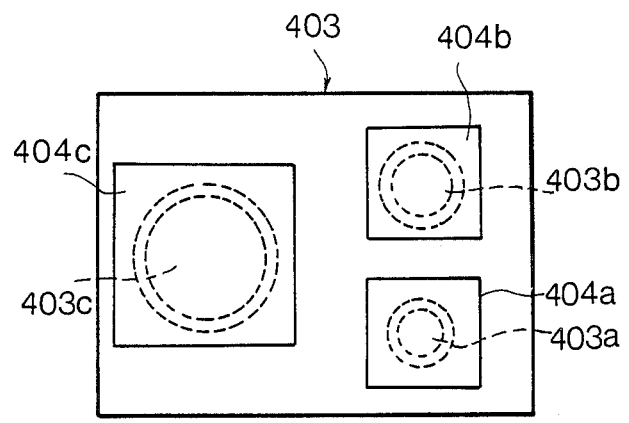
F I G. 11
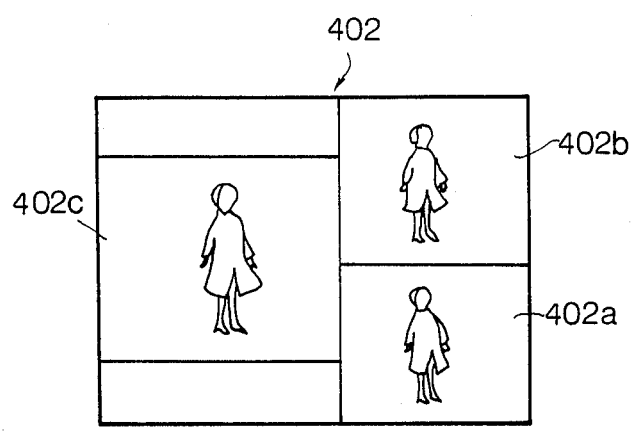
F I G. 12

METHOD OF SPECTROGRAPHICALLY MEASURING DENSITY OF PHOTOGRAPHIC NEGATIVE COLOR FILM

BACKGROUND OF THE INVENTION

1. Field of the Invention

The present invention relates to a method of spectrographically measuring density of a strip of photographic negative color film with images recorded thereon and more particularly to a method of spectrographically measuring density of a strip of photographic negative color film which is suitably employable for exposure control of a photographic printing machine in which images recorded on a strip of photographic negative color film are printed on photographic printing paper.

2. Description of the Prior Art

As is well known to any expert in the art, a photographic printing machine (hereinafter referred to as printer) in which images on a strip of photographic negative color film obtained under various image taking (photographing) states or exposure conditions are printed on photographic printing paper (hereinafter referred to printing paper) is provided with control means which comprises an exposure control circuit and others in order to assure that the printer is operated under the optimum exposure conditions which are obtained by way of the steps of spectrographically measuring relative density, degree of saturation, average density or the like of the negative and then correctively determining exposure conditions for the printer in consideration of the results of measurement made in that way as well as photographic properties inherent to a printing paper to be used. Thus, printing operation is performed automatically by operating the printer.

Incidentally, the conventional method of spectrographically measuring density of a negative of the above-mentioned type is normally carried out by way of the steps of projecting an image recorded on a negative on light beam receiving faces of photoelectrical light beam receiving means with the aid of a plurality of projection optical systems including color filters for three primary colors and then making integration comparison with respect to output of each of the photoelectrical light beam receiving means.

However, it has been pointed out that a drawback with the conventional method of the above-mentioned type is that proper exposure conditions cannot be obtained with respect to a negative on which so-called density failure or color failure occurs (i.e., abnormal density or color distribution, such as too dark or too light) because only average value is obtainable over the whole image on a negative when the conventional method is employed for the intended purpose.

To obviate the foregoing drawback, a proposal has been made for improving the conventional method of spectrographically measuring density in such a manner that a negative having images recorded thereon is divided into a plurality of smaller divisional faces, the thus-divided faces are scanned and density is measured with respect to each of the smaller divisional faces whereby the optimum exposure conditions are obtained. However, the proposed method also has the drawback that a scanning portion becomes excessively large and complicated in structure due to the necessity for utilization of a light beam. This leads to a result that an apparatus for carrying out the method is expensive to manufacture.

SUMMARY OF THE INVENTION

Hence, the present invention has been made with the foregoing background in mind and its main object resides in providing a method of spectrographically measuring density of a strip of photographic negative color film of the type which assures that hue, degree of saturation and average density can be measured with respect to each of smaller divisional light beam receiving faces very quickly with high accuracy compared with the conventional method using a single projection optical system for a single projection image.

Other object of the present invention is to provide a method of spectrographically measuring density of a strip of photographic negative color film of the type which assures that the method can be carried out simply without any occurrence of density failure and color failure and an apparatus for carrying out the method can be operated easily and manufactured at an inexpensive cost.

Another object of the present invention is to provide a method of spectrographically measuring density of a strip of negative color film of the type which assures that exact exposure conditions can be easily obtained very quickly without any necessity for trial and error and without any occurrence of error attributable to differences in the skill of operator.

Further, another object of the present invention is to provide a method of spectrographically measuring density of a strip of photographic negative color film of the type which assures that exposure conditions can be determined automatically.

Still further, another object of the present invention is to provide a method of spectrographically measuring density of a strip of photographic negative color film of the type which can be simply applied to a printer without any particular difficulty.

To accomplish the above objects there is proposed, according to the present invention, a method of spectrographically measuring density of a strip of photographic negative color film which comprises the steps of concurrently projecting an image of the photographic negative color film with certain image recorded thereon on each of a plurality of smaller divisional light beam receiving faces on an image receiving element with the aid of a plurality of projection optical systems. The optical systems include color separating means for separating projected light into three primary colors and are equal in number to the number of the smaller divisional light beam receiving faces. The smaller divisional light beam receiving faces are produced by dividing a light receiving face having a large number of photoelectric converting elements distributed thereover in a two-dimensional plane. The method further includes electrically scanning the photoelectric converting elements, converting output signal obtained by electrical scanning on each of the smaller divisional light beam receiving elements and storing it, and measuring relative density, degree of saturation and average density with respect to a part on the photographic negative color film corresponding to each of the smaller divisional light beam receiving faces with reference to thus stored results.

Other objects, features and advantages of the present invention will become more readily apparent from reading of the following description which has been prepared in conjunction with the accompanying drawings.

BRIEF DESCRIPTION OF THE DRAWINGS

The accompanying drawings schematically illustrate a method of spectrographically measuring the density of a strip of photographic negative color film according to the present invention wherein certain parts or components which are readily understood by those skilled in the art have been omitted for the purpose of illustration, wherein

FIGS. 9 and 10 are a view exemplifying a light beam receiving face of a CCD divided into a plurality of smaller divisional light beam receiving faces in accordance with another embodiment of the invention, wherein no projection optical system is shown for the purpose of simplification of illustration.

FIG. 11 is a front view of a projection optical system similar to FIG. 6 in accordance with further another embodiment of the invention.

FIG. 12 is a front view of a light beam receiving face of a CCD similar to FIG. 8 which is divided into three smaller divisional light beam receiving faces by the projection optical system in FIG. 11.

DESCRIPTION OF THE PREFERRED EMBODIMENTS

Figure 1:
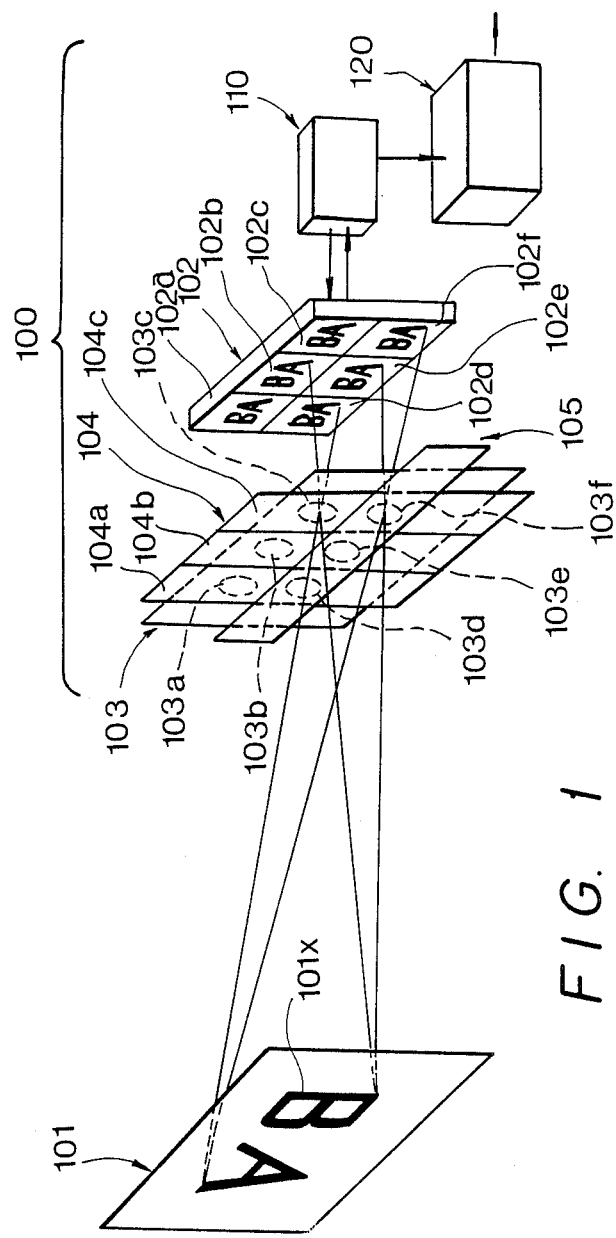
FIG. 1 is a schematic perspective view of an apparatus for carrying out the method of the invention.

Now, the present invention will be described in greater detail hereunder with reference to the accompanying drawings which illustrate preferred embodiments thereof.

First, the present invention will be described with reference to FIG. 1 as to an apparatus for carrying out a method of spectrographically measuring density of a strip of photographic negative color film, wherein the apparatus is identified by reference numeral 100. As will be described in more details later, the method of the invention is carried out by measuring relative density, degree of saturation and average density at each one of a plurality of sections on the photographic negative color film on which images have been already recorded.

As shown in FIG. 1, a lens unit 103 is disposed between a negative 101 havinq images 101x recorded thereon and an image receiving element 102. Element 102 is divided into six sections having receiving surfaces that comprise light beam receiving faces 102a to 102f. It should be noted that a number of photoelectric converting elements that can be conventional charge coupled devices (CCD) are uniformly arranged over the two-dimensional surface of the image receiving element 102. The lens unit 103 includes lenses 103a to 103f. A color filter unit 104, which serves as a color separating means, is disposed forwardly of the lens unit 103. Specifically, a color filter 104a for separating light transmitted through the negative 101 into red color light is disposed forwardly of the lens 103a, a color filter 104b for separating transmitted light into green color light is disposed forwardly of the lens 103b and a color filter 104c for separating transmitted light into blue color light is disposed forwardly of the lens 103c. Further, a combination of color filter 104a and an ND (or Neutral Density) filter 105 is disposed forwardly of the lens 103d, a combination of color filter 104b and an ND filter is disposed forwardly of the lens 103e, and a combination of color filter 104c and ND filter 105 is disposed forwardly of the lens 103f. The ND filters have a density as represented by the letter "N". Thus, a plurality of projection optical systems including color separating means and light beam intensity changing means as mentioned above are provided in accordance with the present invention. The projection optical systems serve to form a projected image of the negative 101 on the light beam receiving faces 102a, 102b and 102g of the image taking element 102 in which the projected image transmitted from the negative 101 is separated into three color components. Further, the projection optical systems serve to form projected images of the negative 101 on the light beam receiving faces 102d, 102e and 102f of the image taking element 102 wherein the projected image transmitted from the negative 101 is separated into three color components and has different transmittance density. It should be added that the above-mentioned projected images are built at the same time.

As clock pulses are supplied from A drive or control unit 110 supplies clock pulses to image receiving element 102 for the purpose of clocking out video signals from the light beam receiving faces 102a to 102f. The video signals correspond to density and hue of the projected image in a synchronized relationship relative to two-dimensional electric scanning of the photoelectric converting elements on the image receiving element 102.

Each of the light beam receiving faces 102a, 102b and 102c is divided into the same number of smaller divisional light beam receiving faces or pixels. A read out signal is transmitted to a signal converting and storing circuit 120 for each of the smaller divisional light beam receiving faces. If the relative density of red color light, green color light and blue color light for each pixel "i" is represented by R(i), G(i) and B(i), hue (i), saturation degree (i) and average density (i.e., the neutral transmittance density) D(i) can be represented, for instance, by the following three formulas.

$$\theta(i) = \tan^{-1}\left[\frac{\frac{1}{2}B(i) - G(i) + \frac{1}{2}R(i)}{\frac{\sqrt{3}}{2}B(i) - \frac{\sqrt{3}}{2}R(i)}\right] \quad (1)$$

$$\gamma(i) = \quad (2)$$

$$\sqrt{\left[\frac{\sqrt{3}}{2}B(i) - \frac{\sqrt{3}}{2}R(i)\right]^2 + \left[\frac{1}{2}B(i) - G(i) + \frac{1}{2}R(i)\right]^2}$$

$$D(i) = \frac{B(i) + G(i) + R(i)}{3} \quad (3)$$

Each of the light beam receiving faces 102d, 102e and 102f is further divided into the same number of smaller divisional light beam receiving faces as in the case of the light beam receiving faces 102a, 102b and 102c in a similar manner. Because ND filter 105 has a density as represented by N and is disposed forwardly of the filter unit 104, the relative density of red color light, green color light and blue color light can be represented in the following manner for each of the "i" smaller divisional light beam receiving faces:

R(i)+N, G(i)+N, B(i)+N

In this case hue and saturation degree of each of the smaller divisional light receiving faces becomes identical to those in the case of smaller divisional light beam receiving faces of the light beam receiving faces 102a, 102b and 102c. Thus, average density D1(i) can be represented by the following formula:

$$D1(i) = \frac{R(i) + G(i) + B(i)}{3} + N \quad (4)$$

It should be noted at "i" in the above formula identifies a certain position among each of smaller divisional light beam receiving faces.

Thus, hue, saturation degree and average density can be calculated for the whole area of each of the smaller divisional light beam receiving faces in accordance with the calculation formulas as exemplified above. Correction can thereby be properly made for damaged or improper negatives with a resulting density failure or color failure until a proper exposure condition is established.

Figure 2:
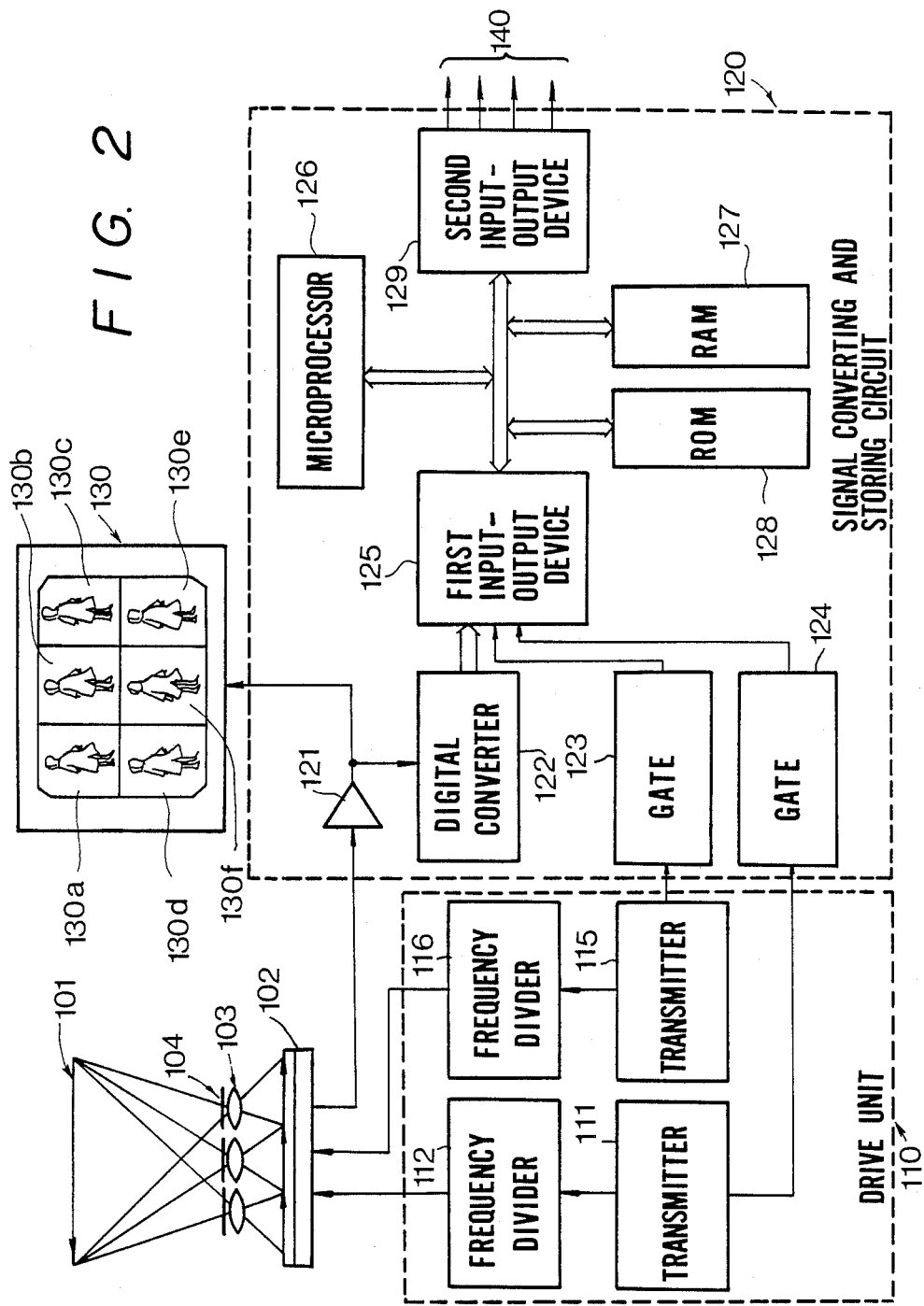
FIG. 2 is a block diagram of the apparatus in FIG. 1, particularly illustrating how the apparatus is operated.

In the apparatus 100 described above with reference to FIG. 1, image receiving element can be a CCD (a video charge coupled device which is hereinafter also identified by numeral 102) and can comprise a number of light beam receiving elements. A more detailed description will be made below as to the structure of apparatus 100 with reference to FIG. 2, in which the same or similar components to those shown in FIG. 1 are identified by the same reference numerals.

The apparatus 100 includes a drive or control unit 110 which essentially comprises a transmitter III adapted to generate a signal having a frequency three times as great as the desired horizontal scanning frequency, fh. Drive unit 110 also comprises a frequency divider 112 for dividing the frequency of the transmitter 111 down to a level of one-third, a transmitter 115 which generates a signal having a frequency two times as great as the desired vertical scanning frequency fv, and a frequency divider 116 for dividing the frequency of the transmitter 115 down to a level of one-half. Output of the drive unit 110 is a clock pulse VclK used to produce a read out in the vertical direction and a clock pulse HclK used to produce a read out in the horizontal direction when the clock pulses are applied to CCD 102.

Signal converting and storing circuit 120 essentially comprises a video frequency amplifier 121 for amplifying video signal transmitted from CCD 102, an N-bit analog-to-digital converter 122, gates 123 and 124, a microprocessor 126 which controls the operation of the system and is usable for making decisions and judgments, a first input-output device 125, a RAM 127 and a ROM 128 which store a computer program used by microprocessor 126 and a second input-output device 129.

The output of CCD 102 is read out by means of a horizontal clock pulse and a vertical clock pulse and is amplified in the video frequency amplifier 121. The amplified output of CCD 102 is applied to a CRT 130 and is applied to converter 122. The output from converter 122 in the form of an N-bit digital signal is applied to an I/O port of the first input-output device 125. Further, the outputs of both 2fv frequency transmitter 115 and 3fh frequency transmitter 111 are also applied to an I/O port of the first input-output device 125 via the gates 123 and 124, respectively. Thus, a constant timing relation is maintained. The output of first device 125 is stored in RAM 127.

Figure 3:
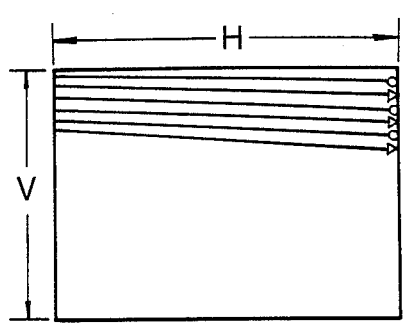
FIG. 3 is a view illustrating horizontal scanning in accordance with a TV scanning system.
Figure 4:
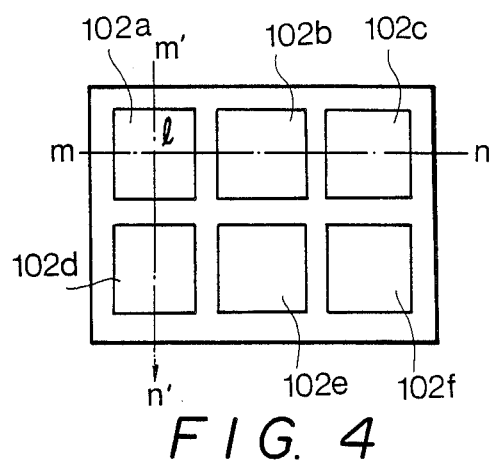
FIG. 4 is a view exemplifying a light beam receiving face on a charge coupled device or CCD divided into a plurality of smaller divisional light beam receiving faces.
Figure 5:
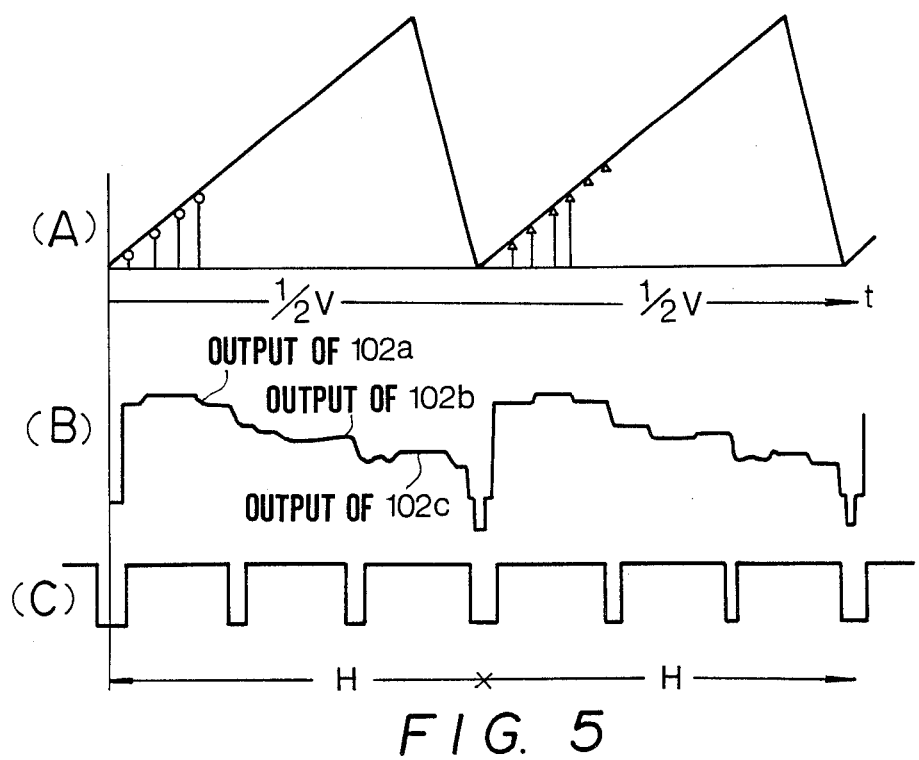
FIGS. 5(A) to (C) are graphs respectively, particularly illustrating the timing relation of output signals during scanning in both the horizontal and vertical directions.

FIGS. 3, 4 and 5 illustrate correlation among the above-mentioned signals. FIG. 3 is an illustrative view showing how scanning is effected over the light beam receiving surface of CRT 130. FIG. 4 is an illustrative view showing how a correlation is established between each of the areas where a projected image is formed on the light beam receiving surface of CCD 102 which has a number of light beam receiving elements distributed thereon. Vertical and horizontal scanning signals are shown superimposed on the light receiving elements. FIGS. 5(A) to (C) are graphs showing the relation between the scanning signals and the projected image read out signal respectively. The abscissas of the graphs serve as the time axis.

Specifically, FIG. 3 shows a plurality of horizontal scanning lines in the case where so-called scanning is effected. As is apparent from the drawing, the horizontal scanning lines comprise two kinds of lines, one of them having a small circle mark at the right end and the other one having an arrow mark at the right end. In this case the time that elapses during vertical scanning amounts to one-half of the normal vertical scanning time V, that is, ½VC. As shown FIG. 4, first scanning is achieved between m' and n' within a period of time of ½V. As will be described later, this may be considered as scanning which is achieved within a period of time of V.

Referring to FIG. 4 again, horizontal scanning between m and n is effected at point l which is located on the vertically scanned line extending between m' and n'. The output obtained during scanning between "m" and "n" has a wave-form as shown in FIG. 5(B). As is apparent from the drawing, the output is successively obtained in accordance with the order of projected images on the light beam receiving faces 102a, 102b and 102c and this output can be separately received by the first input-output device 125 and stored in RAM 127. Output of the light beam receiving faces 102d, 102e and 102f can be obtained in the same manner.

Next, the data concerning two-dimensional distribution of density on each of the light beam receiving faces 102a to 102f are read out and a decision is then made by the programmed read out data with the aid of a microprocessor 126 on the basis of the read out data whether correction is required. If correction is required, control signals are generated for moving in-out control of correction filter and controlling exposure time. The control signals are transmitted to an exposure control circuit via signal lines 140 through second input-output device 129.

The present invention has been described above with respect to the embodiment whereby data concerning the light beam receiving faces 102a to 102f is generated and stored for each of the light beam receiving faces 102a to 102f. However, the present invention should not be limited only to this. Alternatively, data concerning the whole light beam receiving surface may be stored successively in a memory so that each of addresses read out by designating a certain address in RAM 127 in accordance with a software program.

Next, another embodiment of the present invention will be described with reference to FIGS. 6 to 8. In this embodiment it is possible to give a heavier weight on the decision being made by utilizing a light beam receiving face having a larger area. In this embodiment, a judgment is made with respect to the neutral transmittal density where the light beam receiving faces of a light receiving element 202 constituting the apparatus 200 are different from one another in size. The judgment is made as to proper exposure for reproducing details of a projected image having an increased resolvability. It should be noted that the similar components in FIGS. 6 to 8 to those in the foregoing embodiment are identified by reference numerals that are 100 greater than those in FIG. 1 for the purpose of simplification of description.

Figure 6:
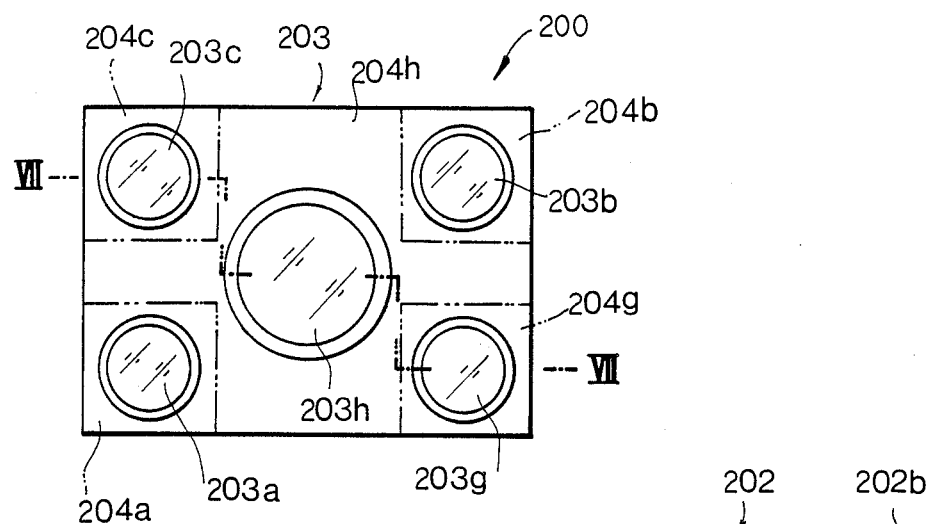
FIG. 6 is a front view of a projection optical system in accordance with another embodiment of the invention.
Figure 8:
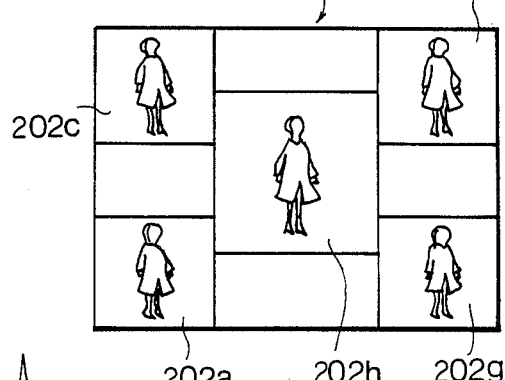
FIG. 8 is a front view of a light beam receiving face of a CCD which is divided into five smaller divisional light beam receiving faces by the projection optical system in FIG. 6.
Figure 7:
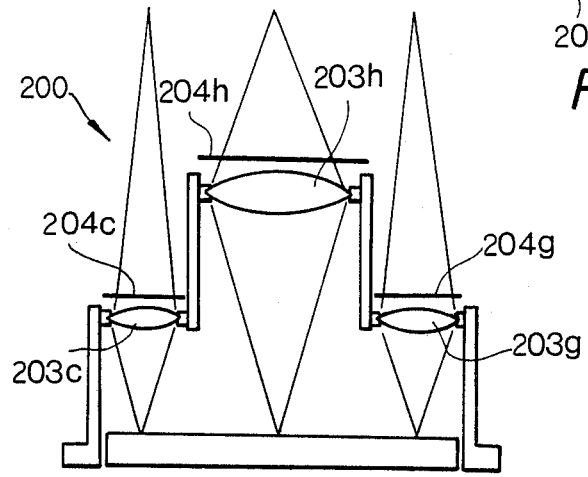
FIG. 7 is a cross-sectional view of the projection optical system taken in line VII—VII in FIG. 6.

FIG. 6 is a view of a projection optical system in the apparatus 200 as seen from the front, FIG. 7 is a cross-sectional view of the projection optical system taken in line VII—VII in FIG. 6, and FIG. 8 is a view illustrating a plurality of light beam receiving faces on (CCD) element 202 which are different in size from one another. As is apparent from the drawings, the apparatus 200 includes a lens unit 203 comprised of five lenses 203a, 203b, 203c, 203g and 203h. The diameter of lens 203h is larger than that of the other four lenses. The diameter and length of a lens holder can be changed in dependence on the diameter of each of the lenses and the focal length.

In the drawings reference numeral 204g designates an ND filter having a density of $+1.0$, and reference numeral 204h designates an ND filter having a desired density of N for obtaining neutral transmittance density.

As will be apparent from description with respect to the foregoing embodiment, the projected image which is transmitted through the color filters 204a, 204b and 204c for separating the projected light into red, green and blue color light, as well as the ND filter having density of $+1.0$, is mounted on the divisional light beam receiving faces 202a, 202b, 202c and 202g. Another projection image for obtaining neutral transmittance density is built on the larger light beam receiving face 202h. In this embodiment, face 202h is located at the central part of the image receiving element 202. Specifically, an area of face 202h is larger than that of the other, peripheral, light beam receiving faces 202a, 202b, 202c and 202g. Further, since face 102h has a larger number of small photoelectric converting elements, it has an improved resolution and thus it is possible to determine exposure time with higher accuracy.

Next, description will be made below as to another embodiment of the present invention with reference to FIGS. 9 and 10. In this embodiment, those elements corresponding to the aforedescribed elements in FIG. 1 have numerals that are greater by two hundred. FIG. 9 illustrates the case where a projected image transmitted through red, green and blue color separating filters illuminates the light beam receiving faces 302, 302b and 303c. The density on each one of faces 302a, 302b and 302c is measured while neutral transmittance density on the light beam receiving face 302h is provided. FIG. 10 illustrates a simplified arrangement of the light beam receiving faces 302a, 302b, 302c and 302h, FIGS. 11 and 12 illustrate another simplified arrangement of the light beam receiving faces.

In this embodiment, those elements corresponding to the aforedescribed elements in FIG. 1 have numerals that are greater by three hundred. However, in this embodiment the light beam receiving face 302h as described above with reference to FIG. 9 is eliminated. FIG. 11 is a front view of a projection optical system similar to FIG. 6 wherein the projected image is built on the light beam receiving faces 402a, 402b and 402c as shown in FIG. 12.

According to any one of the above-described embodiments, the method of the invention is carried out by the steps of separating colors from a projected image built on each of a plurality of light beam receiving faces by using red, green and blue color light filters and light which is transmitted through neutral transmittance density filter. Thereafter hue, saturation degree and average density for each of smaller divisional light beam receiving faces are calculated with the above-noted formulas (1) to (4) and the optimum exposure condition is determined.

Further, each of the above-described embodiments has been described as to the case where a CCD is employed as the image receiving element. However, the present invention should not be limited only to this. Alternatively, electronic tube type and semiconductor type elements having light beam receiving faces arranged in the two-dimensional manner may be employed as image taking element without any loss in function and effect.

Figure 13:
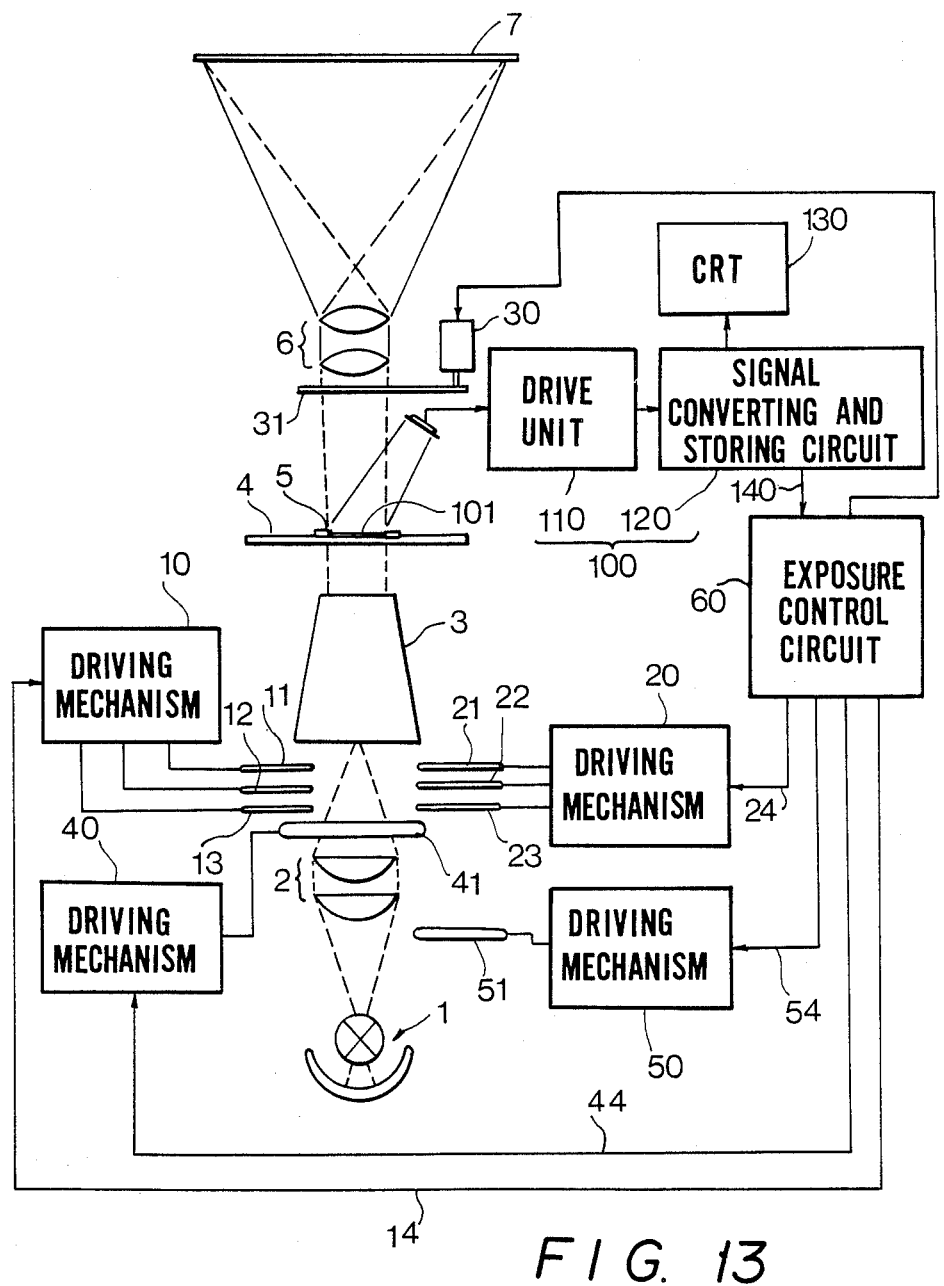
FIG. 13 is a schematic view of a printer in which the apparatus for carrying out the method of the invention is incorporated, particularly illustrating how the printer is constructed.

Finally, with reference to FIG. 13, description will be made below of a printer incorporating the apparatus 100 (or one of the other embodiments) for carrying out the present invention incorporated therein. FIG. 13 schematically illustrates how components constituting the printer are arranged in the printer. In the drawing reference numeral 1 designates a light source. Light beams emitted from the light source 1 are projected onto an original mounting board 4 via a condenser 2 and a mixing unit 3. An image 101x in a negative film 101 placed on a format mask 5 on board 4 is projected onto a positive surface 7 via a lens 6. Surface 7 is fitted with printing paper which is fed from a feeding device (not shown) and printing of the image 101x is achieved by opening and closing a shutter 31 adapted to be actuated by a shutter driving device 30.

The apparatus 100 is provided with appropriate projection optical systems, and is located at the position behind the original mounting board 4, outside the path of the main light beam which is depicted in dashed lines and in the area where scattered light is existent. The path of the light beam used by apparatus 100 is shown by solid lines. Signals generated in the apparatus 100 are transmitted to an exposure control circuit 60.

Further, signals processed in the exposure control circuit 60 are transmitted via a connecting line 14 to a driving mechanism 10 which serves to insert complementary color filters 11, 12 and 13 into the light passage located before the mixing unit 3. The signals are also transmitted via a connecting line 24 to a driving mechanism 20 used to insert color filters 21, 22 and 23, and are transmitted via a connecting line 44 to a driving mechanism 40 used to insert a dichroic calibration filter 41 (correction filter). Further, the signals are also transmitted via a connecting line 54 to a driving mechanism 50 used to insert a heat protection filter 51. Finally, reference numeral 130 designates a CRT or video monitor which is used to confirm whether a projected image is existent or not.

As is apparent from the above description, the method of the invention is carried out by way of the steps of dividing the light beam receiving face on a single image taking element having a number of photoelectric converting elements distributed thereover into a plurality of smaller divisional light beam receiving faces with the aid of a plurality of projection optical systems including color separating means and light beam intensity changing means as required, performing color separation of image recorded on the photographic negative color film on each of the smaller divisional light beam receiving faces providing a projected image having a difference in the density on each of the smaller divisional light beam receiving faces, electrically scanning the faces to convert the photographic image into electrical signals, storing the signals and then measuring density by making comparison among the results of scanning for each of the smaller divisional light beam receiving faces. As a result of the characterizing features of the method of the invention as mentioned above, it is possible to calculate and measure hue, saturation degree and average density for each of the smaller divisional light beam receiving faces very quickly with a high degree of accuracy as compared with the conventional method which is carried out with a single projection image using a single projection optical system. Thus, by employing the method of the invention for a printer it becomes possible to operate the printer without any occurrence of density failure and color failure.

While the present invention has been described above with respect to a few preferred embodiments thereof, it should of course be understood that the present invention should not be limited only to them but that various changes or modifications may be made in any acceptable manner without departure from the spirit and scope of the invention as defined by the appended claims.

What is claimed is:

1. A method of spectrographically measuring density of a strip of photographic negative color film comprising the steps:

concurrently projecting images of said photographic negative color film having a certain image recorded thereon on each of a plurality of smaller divisional light beam receiving faces of an image receiving element using a plurality of projection optical systems including color separating means for separating projected light into three primary colors, the number of said smaller divisional light beam receiving faces being equal to that of said projection optical systems, said smaller divisional light beam receiving faces having a large number of photoelectric converting elements distributed thereover in a two-dimensional manner, each element providing an output signal when scanned;

electrically scanning said photoelectric converting elements;

converting said output signal to a digital signal;

storing said digital signal; and measuring relative density, degree of saturation and average density with respect to a part on the photographic negative color film corresponding to each of the smaller divisional light beam receiving faces with reference to thus stored results.

2. A method as defined in claim 1, wherein the size of each of the smaller divisional light beam receiving faces is different from the other faces so as to produce a difference in resolvability of the image on the photographic negative color film.

3. A method of spectrographically measuring density of a strip of photographic negative color film comprising the steps:

concurrently projecting images of said photographic negative color film having a certain image recorded thereon on each of a plurality of smaller divisional light beam receiving faces of an image receiving element using a plurality of projection optical systems including color separating means for separating projected light into three primary colors and a further plurality of projection optical systems including further color separating means which are the same as those in the first-mentioned projection optical systems and having light beam intensity changing means added to said further color separating means, the number of said smaller divisional light beam receiving faces being equal to that of the two projection optical systems, said smaller divisional light beam receiving faces having a large number of photoelectric converting elements distributed thereover in a two-dimensional manner, each element providing an output signal when scanned;

electrically scanning said photoelectric converting elements;

converting said output signal to a digital signal;

storing said digital signal; and measuring relative density, degree of saturation and average density with respect to a part of the photographic negative color film corresponding to each of the smaller divisional light beam receiving faces with reference to thus stored results.

4. A method as defined in claim 3, wherein the size of each of the smaller divisional light beam receiving faces is different from the other faces so as to produce a difference in resolvability of the image on the photographic negative color film.

5. A method of spectrographically measuring density of a strip of photographic negative color film comprising the steps:

concurrently projecting images of said photographic negative color film having a certain image recorded thereon each of a plurality of smaller divisional light beam receiving faces of an image receiving element using a plurality of projection optical systems including color separating means for separating projected light into three primary colors and further a plurality of projection optical systems including only light beam intensity changing means, the number of said smaller divisional light beam receiving faces being equal to that of the two projection optical systems, said smaller divisional light beam receiving faces having a large number of photoelectric converting elements distributed thereover in the two-dimensional manner, each element providing an output signal when scanned;

electrically scanning said photoelectric converting elements;

converting said output signal to a digital signal;

storing said digital signal; and measuring relative density, degree of saturation and average density with respect to a part of the photographic negative color film corresponding to each of the smaller divisional light beam receiving faces with reference to thus stored results.

6. A method as defined in claim 5, wherein the size of each of the smaller divisional light beam receiving faces is different from the the other faces so as to produce a difference in resolvability of the image on the photographic negative color film.

7. A method of spectrographically measuring density of a strip of photographic negative color film comprising the steps:

concurrently projecting images of said photographic negative color film having a certain image recorded thereon on each of a plurality of smaller divisional light beam receiving faces of an image receiving element using a plurality of projection optical systems including color separating means for separating projected light into three primary colors, said photographic negative color film being set onto a format mask on an original holding board in a printer, the number of said smaller divisional light beam receiving faces being equal to that of said projection optical systems which are disposed outside of the light beam passage of an exposing and printing light beam emitted from a light source for printing the image of the photographic negative color film and in the area where the exposing and printing light beam is propagated, said smaller divisional light beam receiving faces having a large number of photoelectric converting elements distributed thereover in a two-dimensional manner, each element providing an output signal when scanned;

electrically scanning said photoelectric converting elements;

converting said output signal to a digital signal;

storing said digital signal; and measuring relative density, degree of saturation and average density with respect to a part on the photographic negative color film corresponding to each of the smaller divisional light beam receiving faces with reference to thus stored results.

8. A method as defined in claim 7 wherein the size of each of the smaller divisional light beam receiving faces is different from the other faces so as to produce a difference in resolvability of the image on the photographic negative color film.

9. A method of spectrographically measuring density of a strop of photographic negative color film comprising the steps:

concurrently projecting images of said photographic negative color film having a certain image recorded thereon on each of a plurality of smaller divisional light beam receiving faces of an image receiving element using a plurality of projection optical systems including color separating means for separating projected light into three primary colors and a further plurality of projection optical systems including further color separating means which are the same as those in the first-mentioned projection optical systems and having light beam intensity changing means added to said further color separating means, said photographic negative color film being set onto a format mask on an original holding board in a printer, the number of said smaller divisional light beam receiving faces being equal to that of the two projection optical systems which are disposed outside of the light beam passage of an exposing and printing light beam emitted from a light source for printing the image of the photographic negative color film and in the area where exposing and printing light beam is propagated, said smaller divisional light beam receiving faces having a large number of photoelectric converting elements distributed thereover in a two-dimensional manner, each element providing an output signal when scanned;

electrically scanning said photoelectric converting elements;

converting said output signal to a digital signal;

storing said digital signal; and measuring relative density, degree of saturation and average density with respect to a part of the photographic negative color film corresponding to each of the smaller divisional light beam receiving faces with reference to thus stored results.

10. A method as defined in claim 9, wherein the size of each of the smaller divisional light beam receiving faces is different from the other faces so as to produce a difference in resolvability of the image on the photographic negative color film.

11. A method of spectrographically measuring density of a strip of photographic negative color film comprising the steps:

concurrently projecting images of said photographic negative color film having a certain image recorded thereon on each of a plurality of smaller divisional light beam receiving faces of an image receiving element using a plurality of projection optical systems including color separating means for separating projected light into three primary colors and a further plurality of projection optical systems including only light beam intensity changing means, said photographic negative color film being set onto a format mask on an original holding board in a printer, the number of said smaller divisional light beam receiving faces being equal to that of the two projection optical systems which are disposed outside of the light beam passage of an exposing and printing light beam emitted from a light source for printing the image of the photographic negative color film and in the area where exposing and printing light beam is propagated, said smaller divisional light beam receiving faces having a large number of photoelectric converting elements distributed thereover in a two-dimensional manner, each element providing an output signal when scanned;

electrically scanning said photoelectric converting elements;

converting said output signal to a digital signal storing said digital signal; and measuring relative density, degree of saturation and average density with respect to a part on the photographic negative color film corresponding to each of the smaller divisional light beam receiving faces with reference to thus stored results.

12. A method as defined in claim 11, wherein the size of each of the smaller divisional light beam receiving faces is different from the other faces so as to produce a difference in resolvability of the image on the photographic negative color film.

* * * * *